(12) United States Patent
Santos et al.

(10) Patent No.: US 10,089,440 B2
(45) Date of Patent: Oct. 2, 2018

(54) PERSONAL HEALTH DATA HUB

(71) Applicant: Signove Tecnologia S/A, Campina Grande, Paraiba (BR)

(72) Inventors: Danilo Freire de Souza Santos, Paraiba (BR); Aldenor Falcao Martins, Paraiba (BR); Andre Felipe de Albuquerque Rodrigues, Paraiba (BR); Jose Luis do Nascimento, Paraiba (BR); Angelo Perkusich, Paraiba (BR); Hyggo Oliveira de Almeida, Paraiba (BR)

(73) Assignee: Signove Tecnologia S/A, Campina Grande (BR)

( * ) Notice: Subject to any disclaimer, the term of this patent is extended or adjusted under 35 U.S.C. 154(b) by 59 days.

(21) Appl. No.: 14/148,548

(22) Filed: Jan. 6, 2014

(65) Prior Publication Data

US 2014/0195263 A1    Jul. 10, 2014

Related U.S. Application Data

(60) Provisional application No. 61/749,821, filed on Jan. 7, 2013.

(51) Int. Cl.
  *G06F 19/00*  (2018.01)
  *G16H 10/65*  (2018.01)
  *G16H 10/60*  (2018.01)

(52) U.S. Cl.
  CPC ........... *G06F 19/323* (2013.01); *G16H 10/65* (2018.01); *G16H 10/60* (2018.01)

(58) Field of Classification Search
  CPC ...... G06Q 50/24; G06Q 50/22; H04B 5/0031; H04B 5/0062; G06F 21/31; G06F 19/322; G06F 19/323; G06F 19/00
  See application file for complete search history.

(56) References Cited

U.S. PATENT DOCUMENTS

| | | | |
|---|---|---|---|
| 2002/0184415 A1 | 12/2002 | Naghavi et al. | |
| 2008/0215627 A1 | 9/2008 | Higgins et al. | |
| 2009/0326981 A1 | 12/2009 | Karkanias et al. | |
| 2012/0095302 A1 | 4/2012 | Adhikari | |
| 2012/0155297 A1 | 6/2012 | Russell et al. | |
| 2013/0109929 A1* | 5/2013 | Menzel | 600/301 |
| 2013/0159008 A1* | 6/2013 | Mills et al. | 705/2 |
| 2013/0282921 A1 | 10/2013 | Tran et al. | |

* cited by examiner

*Primary Examiner* — Maroun P Kanaan
(74) *Attorney, Agent, or Firm* — Schwabe, Williamson & Wyatt, P.C.

(57) ABSTRACT

In various embodiments, a personal health data hub ("PHDH") may include a device that receives health data from personal health devices ("PHDs"), stores the health data, and sends them to personal health records. Health data may be received by PHDH using multiple communication technologies, such as Bluetooth, Bluetooth Low Energy, ANT+, USB, etc. The PHDH may be used by different users such as multiple user sessions. Users may access and control the PHDH through different UI mechanisms. The PHDH may interact with users, such as by indicating states and/or events using light and/or sound indicators. The PHDH may use a wireless collector accessory enabled peripheral device to receive health data from a PHD. The WCA-enabled device may communicate personal health data to the PHDH on behalf of the PHD. Other embodiments are described and claimed.

30 Claims, 6 Drawing Sheets

PERSONAL HEALTH DATA HUB

CROSS-REFERENCE TO RELATED APPLICATION

This application claims the benefit of U.S. Provisional Application No. 61/749,821, entitled "PERSONAL HEALTH DATA HUB FOR MULTIPLE USERS WITH WIRELESS COLLECTOR," filed Jan. 7, 2013. The application is herein incorporated by reference in its entirety.

TECHNICAL FIELD

This disclosure relates, generally, to the field of data processing, and in particular to the use of personal health devices.

BACKGROUND

Technological advances make possible the creation of new portable, affordable, and connectable Personal Health Devices ("PHDs"). These PHDs may collect vital signals of users, such as blood pressure, heart rate, weight, etc., and share these signals in the form of digital data using communications technologies, such as Bluetooth, Bluetooth Low Energy, USB, Near Field Communications ("NFC"), Radio-Frequency Identification ("RFID"), etc.

Some PHDs can be associated and connected to other devices using wired or wireless technologies, such as Bluetooth or USB. These other devices may be called, for example, health gateways, collectors, or hubs, and may generally be referred to as "hubs" herein. These devices may be specific hardware devices for collecting of health data, and/or software applications running on cellphones or computers. These devices may collect data from PHDs and send them to external servers.

In some scenarios, PHDs may not need to be associated and connected to a specific hub in order to collect health data. For example, these PHDs may share their information using near-field technologies in a way that the connection between the PHD and hub may happen in one specific moment, and no association between the devices may be required a priori. The use of near-field technologies may involve the touching, or close physical approach, of the hub to the PHD. This physical movement may be difficult for a user, such as when if the hub or the PHD is not portable enough. For example: the hub may include a personal computer or a set-top box attached to a TV set. In another example, and the PHD may include a weighing scale on the floor, which is not easily moved.

In various scenarios, the use of hubs and PHDs may make it possible to users to record health information and take care of their health at home, work or other places. However, although they are Personal Health Devices, a common use case is that PHDs are used by multiple users. As an example, a weighing scale at home may be shared by a whole family. Therefore, associating or connecting a PHD to one's personal device, such as a cellphone, or other device used as a hub, may make this PHD accessible only to the owner of the cellphone.

BRIEF DESCRIPTION OF FIGURES

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

As used herein, the term "device" may refer to, be part of, or include an Application Specific Integrated Circuit ("ASIC"), an electronic circuit, a processor (shared, dedicated, or group) and/or memory (shared, dedicated, or group) that execute one or more software or firmware programs, a combinational logic circuit, and/or other suitable components that provide the described functionality.

In the context of this disclosure, a user may be a person that uses the health data hub to collect health or wellness related data from personal health devices ("PHDs"). A personal health data hub ("PHDH") may include a device that receives PHD data using wireless or wired communication technologies and associates this data to a specific user. Association of data may include storage of the received data as owned by one user. The PHDH may, in various embodiments, send this data to external databases or not.

Figure 1:
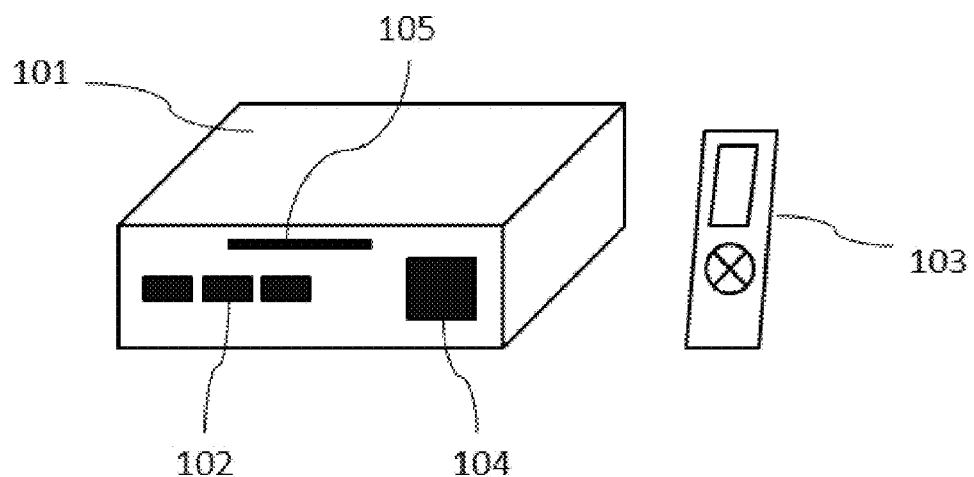
FIG. 1 illustrates an example set of devices that may be included in a personal health device hub ("PHDH"), in accordance with various embodiments.

Referring now to FIG. 1, a PHDH may, in various embodiments, include a central device 101 with communication interfaces 102, such as Universal Serial Bus ("USB"), WiFi, Ethernet, ANT+ or Bluetooth. The PHDH may also include a peripheral device 103 that may include a wireless collector accessory ("WCA"). The central device may, in various embodiments, have a video output interface 104, and may have a RGB (Red-Green-Blue) light indicator 105, or other type of indicator. The peripheral device 103 may incorporate various form factors, including, but not limited to, a remote control, a pen, or a card.

Figure 5:
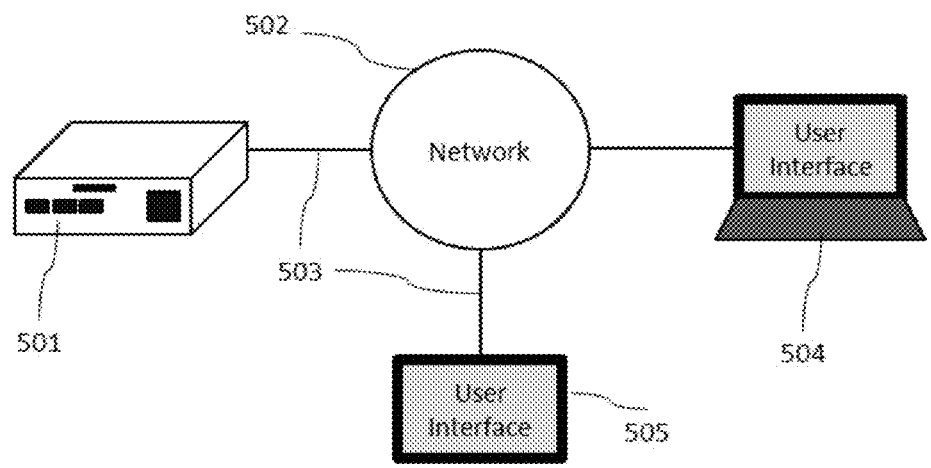
FIG. 5 illustrates examples of access of the PHDH user interface by multiple devices in a network, in accordance with various embodiments.

FIG. 5 illustrates how a PHDH central device may be connected to a network 502 such as using a communication link 503. A network may include, in various embodiments, a direct Internet connection or a Local Area Network (LAN). In various embodiments, PHDH central device may not be connected to a network while still incorporating various techniques and embodiments described herein.

The PHDH device may, in various embodiments, be configured to manage user sessions in order to know who is using a PHD at a particular time. In various embodiments, various authentication methods may be used to identify a user.

In a first method, the user may be authenticated with the PHDH remotely, such as, for example, using a remote control. Using this method, the user may enter his/her credentials within the PHDH. Credentials may, in various embodiments, include a username and password or other sequence of characters. Credentials may, in various embodiments, be entered through the pressing of keys through the remote control.

Figure 7:
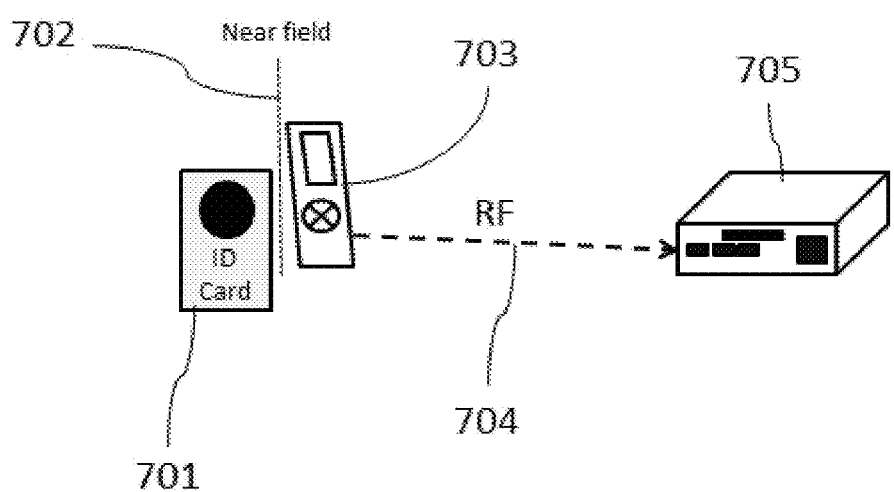
FIG. 7 illustrates how the user may be authenticated through the WCA using near-field enabled identification devices, in accordance with various embodiments.

A second user authentication method may use near-field technologies, such as NFC or RFID, to identify the user. The user may be identified using an identification card, a token, or any other near-field enabled device. FIG. 7 illustrates examples of this authentication method, described in greater detail below.

After the user identification, the user may be considered to have a session opened with the PHDH. During a session, PHD data received by PHDH may be associated to the authenticated user. User associated data may be stored into the PHDH. The PHDH may also forward this data to a remote database called Personal Health Record.

Figure 2:
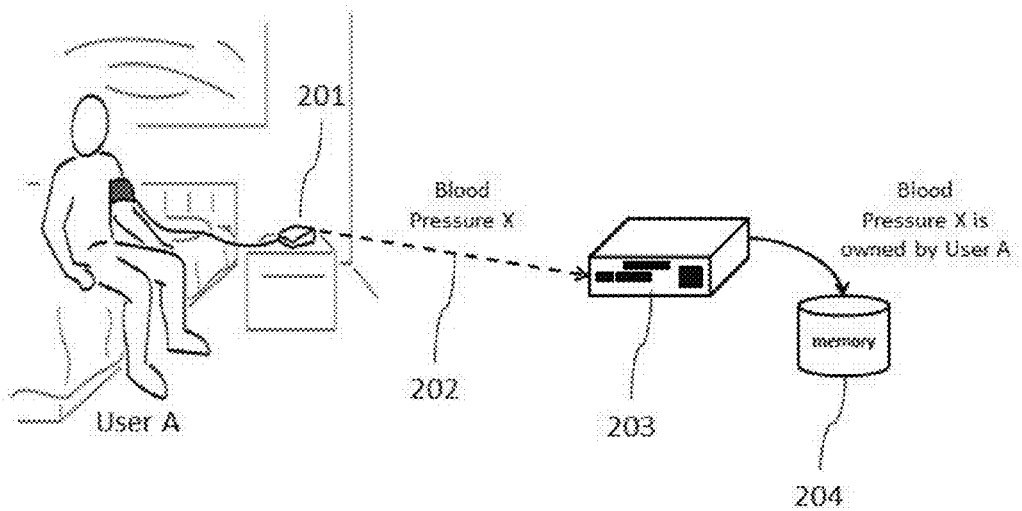
FIG. 2 illustrates examples of use by a user to measure health signals using a PHD, and of sending of data measures to PHDH, in accordance with various embodiments.

Referring now to FIG. 2, an example of a user collecting health measures using a PHD and PHDH is illustrated. In a first step, the user may collect health measures using a PHD 201. As it follows, the PHD may send the measures using a communication link 202 to the PHDH. If the user has started a session on the PHDH 203, measures received by it may be associated to this user and saved on memory 204. Memory, in various embodiments, may include a RAM, ROM, hard drive, solid-state drive, or other storage device inside or associated with the PHDH.

Figure 3:
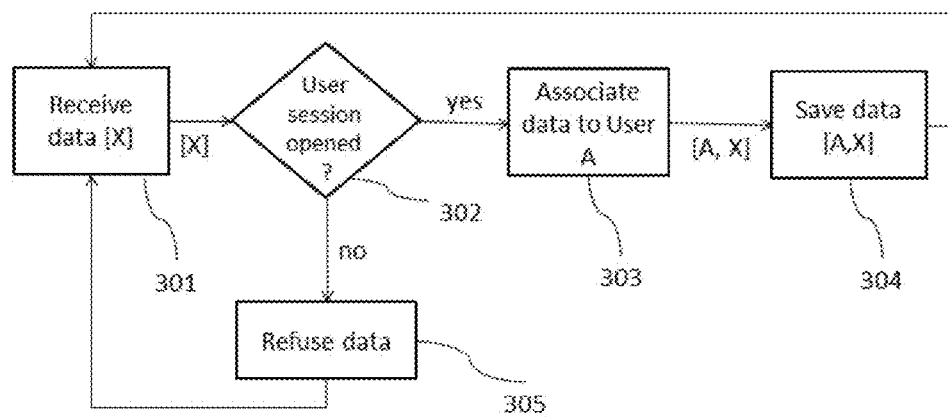
FIG. 3 illustrates an example state diagram relating to how data is associated to a user through an authentication session on PHDH, in accordance with various embodiments.

In various embodiments, association of a health measure [X] to user A may include, when storing a measure, the PHDH creating a tuple where measure [X] is associated with the ID key for user A. FIG. 3 illustrates examples of a sequence flow of a data measure X received by PHDH. The data may be received at block 301. When receiving data through one of its communication links, PHDH may check if any user has a session opened in it at block 302. If a session is opened for user A, PHDH may associate data measure [X] to user A, thus creating a new piece of information [A, X] at block 303. PHDH may then save this information in memory (shared, dedicated, or group) at block 304. If no user is authenticated in PHDH, so, no user session is opened, the measure [X] may be refused in the communication link at block 305.

After a session is opened, the user may logout or exit the authenticated session using a user interface ("UI") associated with the PHDH. Thereafter, the PHDH may accept other users to authenticate and open sessions with it, such as by using previous described methods. In other embodiments, other methods for receipt of a data measure by the PHDH may be utilized.

In various embodiments, multiple modes may be provided for user interaction with the PHDH. User interaction may be made possible, in various embodiments, by the use of UIs. UIs may be accessed or visualized using different devices or software applications. The PHDH may have one or more of the UI mechanisms described herein.

Figure 4:
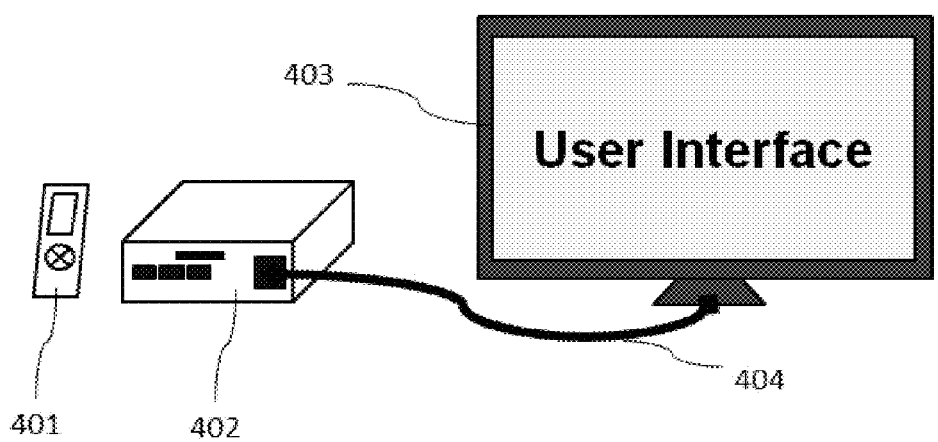
FIG. 4 illustrates examples of setup to access a PHDH user interface using an external display, and control of the PHDH using the peripheral device, in accordance with various embodiments.

Now referring to FIG. 4, an illustration of a first UI method may be found. In various embodiments, the user may visualize the PHDH UI using a Television set or Monitor Screen 403 connected to the PHDH, such as by using a video or multimedia communication link 404. The user may control PHDH central device 402 using a remote control peripheral device 401.

Referring now to FIG. 5, an illustration of a second UI method may be found. In various embodiments, the user may access the PHDH 501 using an Internet Browser application running on a device, including but not limited to a personal computer 504, cellphone, personal digital assistant ("PDA"), tablet 505 and television. In various embodiments, access to the PHDH using an Internet Browser application may include accessibility of the PHDH to devices in the same network 502 of PHDH. The PHDH and other devices may, in various embodiments, be connected to network using wired or wireless communication links 503. A network, in various embodiments, can be a direct connection to the Internet or Local Area Network (LAN).

In various embodiments, access to the PHDH using one or more of the specified interaction modes may enable the user to authenticate and start a session with the PHDH, access his/her personal health information stored into the PHDH, locally or remotely, and perform maintenance operations on PHDH.

FIG. 1 illustrates the PHDH central device 101 and a light indicator 105. This light indicator may, in various embodiments, be one of various kinds of light-emitting devices, such as an LED. The PHDH central device may also have an internal sound-emitting device, such as a beeper device or a speaker. The PHDH central device may use the light-emitting device and sound-emitting device to indicate its state.

The PHDH central device may change the color and/or manner of light emission of the light-emitting device to indicate one or more states and events. The listing of particular states and/or events herein is not intended to limit states or events that may be experienced and/or indicated by the PHDH.

A state where no user has a session started with the PHDH.

A state where one user has a session started with the PHDH.

A state where health data is being received by PHDH.

A state where the PHDH has no network connection.

An event of health data is successfully received by PHDH.

An event of health data is unsuccessfully received by PHDH.

The PHDH central device may also emit a sound using the sound-emitting device to indicate one or more event or states. The listing of particular events herein is not intended to limit states or events that may be experienced and/or indicated by the PHDH.

An event of one user having started a session with the PHDH.

An event of one user having stopped (or left) a session with the PHDH.

An event of health data being successfully received by PHDH.

An event of health data being unsuccessfully received by PHDH.

In various embodiments, the PHDH may receive data from PHDs using different communication technologies, such as, but not limited to, Bluetooth, Bluetooth Low Energy, ANT+, USB, NFC, RFID and Infra-red.

To read data from PHDs that use near-field technologies, such as NFC and RFID, in various embodiments the PHD may be made to touch the PHDH. In various embodiments, a WCA may be embedded in the peripheral device 103 of PHDH. The WCA may be connected to the PHDH using a wireless RF link. The WCA may be used to approach the PHD device, read the PHD's data, such as using near field technology, and forward this data to PHDH, such as using the RF wireless link. The PHDH may, in various embodiments, handle WCA data as a PHD device data. In various embodiments, the data may be associated to one user, stored into the PHDH, and forwarded to a personal health record.

Figure 6:
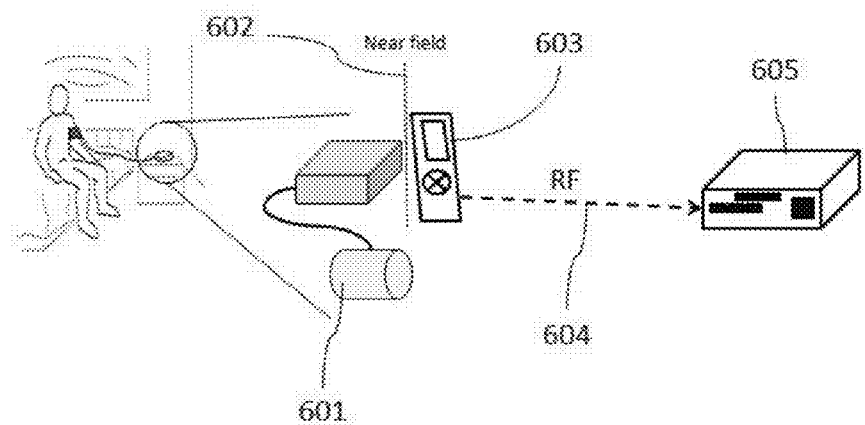
FIG. 6 illustrates how a peripheral device including a wireless connector accessory ("WCA") may be used to read measures from near-field enabled PHD, in accordance with various embodiments.

Referring now to FIG. 6, an example of a WCA-enabled peripheral device usage is illustrated. A PHD 601 may, in various embodiments, have a near-field communication interface 602. WCA peripheral device 603 may approach the near-field area and read measurements from PHD 601, such as using near-field technology. After this reading, WCA-enabled peripheral device 603 may forward measurements to PHDH central device 605, such as by using an established Radio-Frequency (RF) communication link 604 or other communication protocol.

The WCA-enabled peripheral device 603 may forward near-field received data to PHDH central device. In various embodiments, a tunnel may be created between the WCA-enabled peripheral device 603 and the PHDH central device 605. The PHDH central device 605 may receive WCA data as if the near-field interface were used to communicate directly with the PHDH central device 605.

Referring now FIG. 7, the previously-described second authentication method may be illustrated. The user may have a near-field enabled identification card or device 701. When approaching the near-field 702, WCA-enabled peripheral device 703 may read identification information from ID card 701, and may forward this information to the PHDH central device 705, such as using RF wireless link 704. The PHDH 703 may receive this identification information, and may start an authenticated user session.

Figure 8:
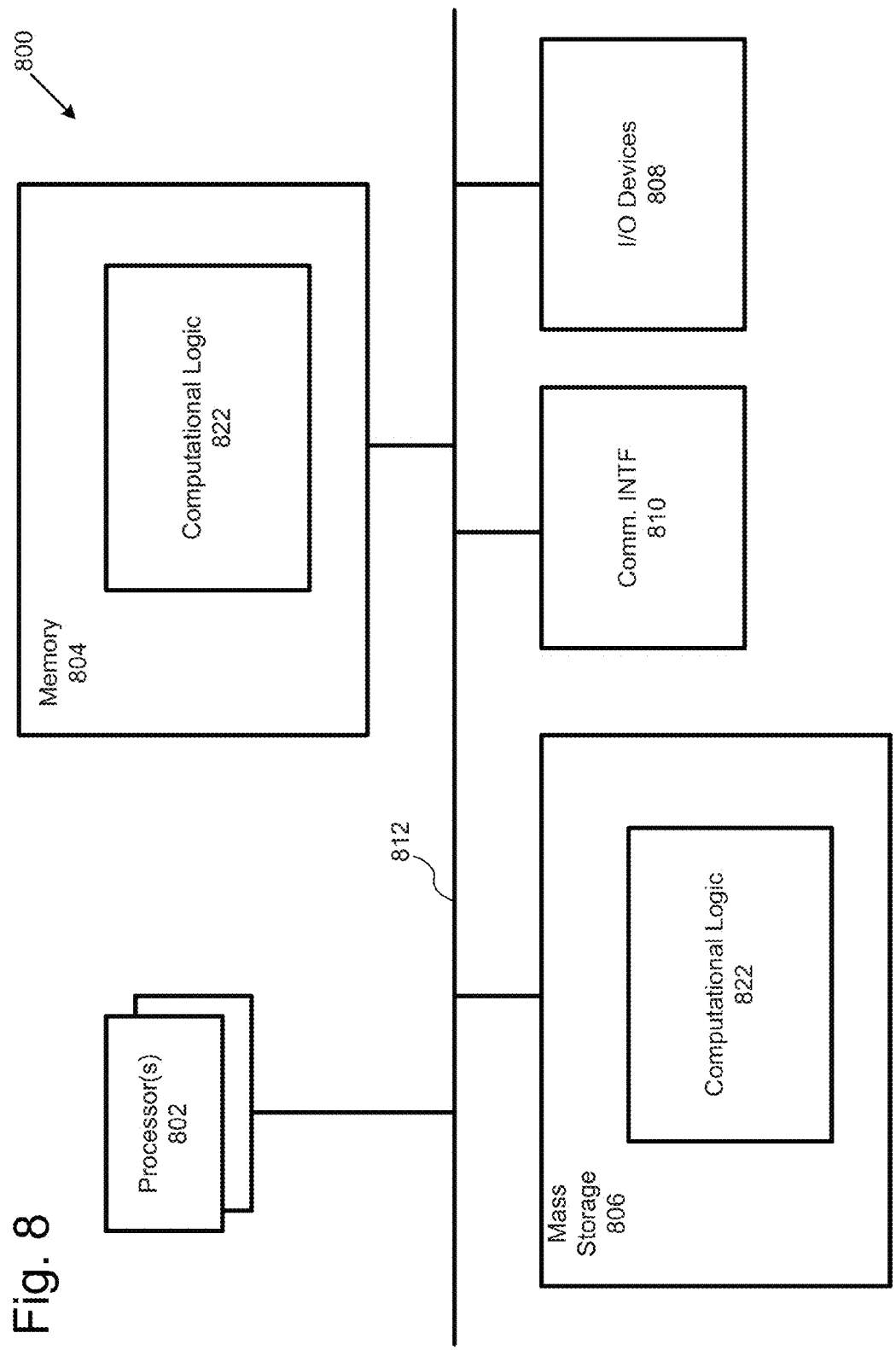
FIG. 8 illustrates an example computing environment suitable for practicing various aspects of the present disclosure, in accordance with various embodiments.

Referring now to FIG. 8, an example computer suitable for use for the arrangements described herein, in accordance with various embodiments, is illustrated. As shown, computer 800 may include one or more processors or processor cores 802, and system memory 804. For the purpose of this application, including the claims, the terms "processor" and "processor cores" may be considered synonymous, unless the context clearly requires otherwise. Additionally, computer 800 may include mass storage devices 806 (such as diskette, hard drive, compact disc read only memory (CD-ROM) and so forth), input/output devices 808 (such as display, keyboard, cursor control and so forth) and communication interfaces 810 (such as network interface cards, modems and so forth). The elements may be coupled to each other via system bus 812, which may represent one or more buses. In the case of multiple buses, they may be bridged by one or more bus bridges (not shown).

Each of these elements may perform its conventional functions known in the art. In particular, system memory 804 and mass storage devices 806 may be employed to store a working copy and a permanent copy of the programming instructions implementing the operations associated with techniques described herein. The various elements may be implemented by assembler instructions supported by processor(s) 802 or high-level languages, such as, for example, C, that can be compiled into such instructions.

The permanent copy of the programming instructions may be placed into permanent storage devices 806 in the factory, or in the field, through, for example, a distribution medium (not shown), such as a compact disc (CD), or through communication interface 810 (from a distribution server (not shown)). That is, one or more distribution media having an implementation of the agent program may be employed to distribute the agent and program various computing devices.

The number, capability and/or capacity of these elements 810-812 may vary, depending on how computer 800 is used and as which device. Their constitutions are otherwise known, and accordingly will not be further described.

Figure 9:
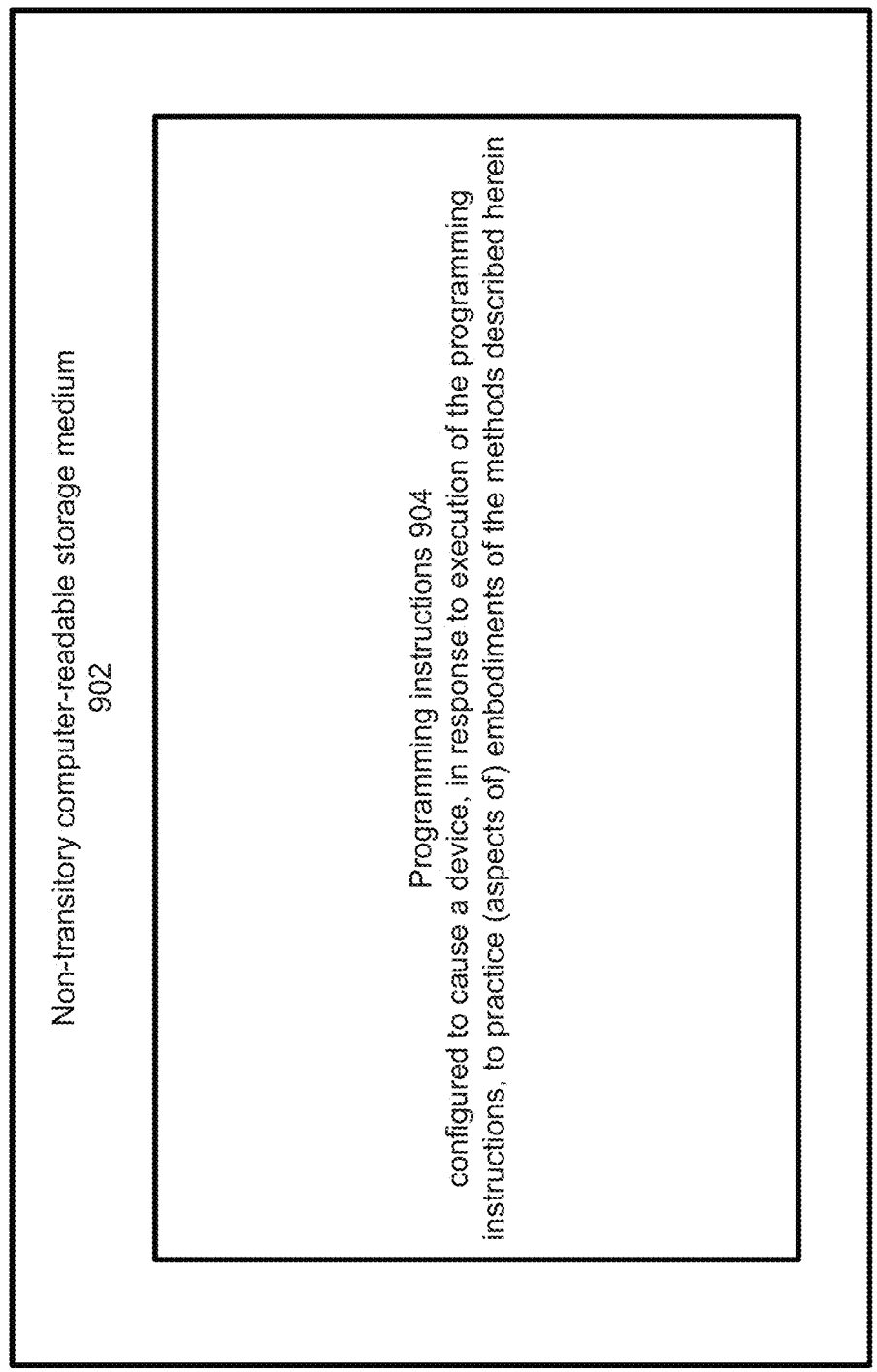
FIG. 9 illustrates an example storage medium with instructions configured to enable an apparatus to practice various aspects of the present disclosure, in accordance with various embodiments.

FIG. 9 illustrates an example non-transitory computer-readable storage medium having instructions configured to practice all or selected ones of the operations earlier described, in accordance with various embodiments. As illustrated, non-transitory computer-readable storage medium 902 may include a number of programming instructions 904. Programming instructions 904 may be configured to enable a device, e.g., computer 800, in response to execution of the programming instructions, to perform, e.g., various operations of processes described above. In alternate embodiments, programming instructions 904 may be disposed on multiple non-transitory computer-readable storage media 902 instead.

Referring back to FIG. 8, for one embodiment, at least one of processors 802 may be packaged together with computational logic 822 configured to practice aspects of processes described herein. For one embodiment, at least one of processors 802 may be packaged together with computational logic 822 configured to practice aspects of processes described herein to form a System in Package (SiP). For one embodiment, at least one of processors 802 may be integrated on the same die with computational logic 822 configured to practice aspects of processes described herein. For one embodiment, at least one of processors 802 may be packaged together with computational logic 822 configured to practice aspects of processes described herein to form a System on Chip (SoC). For at least one embodiment, the SoC may be utilized in, e.g., but not limited to, a computing tablet.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second or third) for identified elements are used to distinguish between the elements, and do not indicate or imply a required or limited number of such elements, nor do they indicate a particular position or order of such elements unless otherwise specifically stated.

We claim:
1. An apparatus for facilitating collection of personal health data, the apparatus comprising:
   one or more computing processors coupled with one or more memory devices, the one or more memory devices to store computational logic;
   the one or more computing processors to implement the computational logic to:
      open individual user sessions for one or more users that are properly authenticated using user authentication data;

collect personal health data of the plurality of users from one or more personal health devices via corresponding communication links between the apparatus and the one or more personal health devices, and control receipt of personal health data from a physically separate collector-accessory-enabled peripheral devices operated by a set of users of the plurality of users via respective radio-frequency ("RF") communication links between the peripheral devices and the apparatus, wherein the received personal health data is obtained by the peripheral devices via Near-Field Communications ("NFC") signaling from personal health devices that are not in direct communication with the apparatus, associate the collected personal health data and the personal health data received from the peripheral device of the one or more users with corresponding user identifiers of the one or more users of the user is an open user session, and refuse the collected personal health data and the personal health data received from the peripheral device of users of the plurality of users that do not have an open user session; and one or more communications interfaces to:

control receipt of the user authentication data from the one or more users of the plurality of users, and control transmission, to a remote data storage device, of the association of the collected personal health data and the personal health data received from the peripheral device with the user identifiers.

2. The apparatus of claim 1, wherein the one or more computing processors to implement the computational logic to open user sessions for receipt of the personal health data of the plurality of users upon receipt of authentication credentials of the plurality of users.

3. The apparatus of claim 2, wherein the one or more computing processors to implement the computational logic to:

obtain the authentication data from the peripheral devices or from a user interface associated with the apparatus; and authenticate the one or more users using the authentication data.

4. The apparatus of claim 3, wherein the one or more computing processors to implement the computational logic to:

obtain the authentication data from the peripheral devices using NFC or Radio-Frequency Identification ("RFID") signaling.

5. The apparatus of claim 1, wherein the personal health data received from the collector-accessory-enabled peripheral devices is obtained from collector cards.

6. The apparatus of claim 1, wherein the one or more computing processors to implement the computational logic to communicate with the collector-accessory-enabled peripheral devices using protocols used to communicate with the one or more personal health devices.

7. The apparatus of claim 1, wherein the one or more communications interfaces to communicate using one or more communications protocols including Bluetooth, Bluetooth Low Energy, ANT+, Universal Serial Bus ("USB"), Near Field Communications ("NFC"), Radio-Frequency Identification ("RFID"), and Infrared communication protocols.

8. The apparatus of claim 7, wherein, to control transmission of the association, the one or more computing processors are to implement the computational logic to instruct the at least one of the one or more communications interfaces to transmit the personal health data associated with the user to the remote data storage device using at least one of the one or more communications protocols.

9. The apparatus of claim 1, wherein the one or more memory devices are to store control logic, and the one or more computing processors are to implement the control logic to facilitate control of the apparatus.

10. The apparatus of claim 9 wherein the one or more computing processors are to implement the control logic to facilitate control of the apparatus using the peripheral device, wherein the peripheral device comprises one or more of: a cellphone, smartphone, tablet computer, personal digital assistant ("PDA"), or a personal computer.

11. The apparatus of claim 9, wherein the one or more computing processors are to implement the control logic to provide a user interface to facilitate control of the apparatus and to facilitate opening and closing of the individual user sessions.

12. The apparatus of claim 11, wherein the one or more computing processors are to implement the control logic to provide the user interface on a television, a monitor screen, or a network browser software application.

13. The apparatus of claim 11, wherein the one or more computing processors are to implement the control logic to communicate with a user interface application for the peripheral device.

14. A computer-implemented method for collecting personal health data, the method comprising:

receiving, by a computer device, user authentication data from one or more users of a plurality of users;

opening by the computer device, individual user sessions for each of the one or more users that are properly authenticated using the user authentication data;

collecting, by the computer device, personal health data of a plurality of users from one or more personal health devices, including receiving personal health data from a collector-accessory-enabled peripheral devices that are physically separate from the computing device and operated by one or more users of the plurality of users, wherein the personal health data is received from the peripheral devices via respective radio-frequency ("RF") communication links between the peripheral devices and the computer device, and wherein the peripheral devices are configured to read personal health data via Near-Field Communications ("NFC") signaling from personal health devices that are not in direct communication with the computing device;

associating, by the computer device, the collected personal health data with a user of the plurality of the one or more users with user identifiers of the one or more users that have an active user session;

discard, by the computer device, the collected personal health data and the personal health data received from the peripheral device of users of the plurality of users that do not have an open user session; and transmitting, by the computer device, the association of the collected personal information with the user identifiers to a remote storage device.

15. The method of claim 14, wherein collecting personal health data comprises:

opening the user session for receipt of personal health data; and collecting personal health data only when a user session has been opened.

16. The method of claim 15, wherein collecting personal health data comprises authenticating users using corresponding peripheral devices.

17. The method of claim 14, wherein the collector-accessory-enabled peripheral devices are further configured to read personal health data from personal health devices that are not configured to directly communicate with the computing device.

18. The method of claim 14, wherein collecting personal health data comprises communicating, by the computer device, with the collector-accessory-enabled peripheral devices using protocols used to communicate with the one or more personal health devices.

19. The method of claim 14, further comprising sending the personal health data associated with the user to the remote data storage device using protocols used to communicate with the one or more personal health devices.

20. The method of claim 14, further comprising facilitating control, by the computer device, of the computer device.

21. The method of claim 20 wherein facilitating control comprises facilitating control via one or more of: a cellphone, smartphone, tablet computer, personal digital assistant ("PDA") or a personal computer.

22. The method of claim 20, wherein facilitating, by the computer device, control comprises providing a user interface to facilitate control of the apparatus.

23. One or more non-transitory computer-readable media comprising instructions written thereon, wherein execution of the instructions by one or more processors of a computer device is to cause the computer device to facilitate collection of personal health data by causing the computer device to:
control receipt of user authentication data from one or more users of a plurality of users;
open individual user sessions for each of the one or more users that are properly authenticated using the user authentication data;
collect personal health data of a plurality of users from one or more personal health devices, wherein to collect the personal health data, the instructions, when executed, cause the computing device to control receipt of personal health data from collector-accessory-enabled peripheral devices that are physically separate from the computing device and operated by one or more users of the plurality of users, wherein the peripheral devices are configured to:
read personal health data via Near-Field Communications ("NFC") signaling from personal health devices that are not in direct communication with the computing device; and
send the read personal health data to the computing device via respective radio-frequency ("RF") communication links;
associate the collected personal health data of the one or more users with a user identifier of the one or more users of the plurality of users whose user session are open;
refuse the collected personal health data and the personal health data of other users of the plurality of users that do not have open user sessions; and
control transmission, to a remote storage device, of the association of the collected personal health data with the user identifiers.

24. The one or more non-transitory computer-readable media of claim 23, wherein, to collect personal health data, execution of the instructions is to cause the computer device to:
open user sessions for receipt of personal health data; and
collect personal health data only when a user session has been opened.

25. The one or more non-transitory computer-readable media of claim 24, wherein, to collect personal health data, execution of the instructions is to cause the computer device to authenticate users using credentials obtained from the peripheral devices.

26. The one or more non-transitory computer-readable media of claim 23, wherein, to collect personal health data, execution of the instructions is to cause the computer device to control communication with the collector-accessory-enabled peripheral devices using protocols used to communicate with the one or more personal health devices.

27. The one or more non-transitory computer-readable media of claim 23, wherein execution of the instructions is to cause the computer device to control transmission of the collected personal health data associated with the user to the remote data storage device using protocols used to communicate with the one or more personal health devices.

28. The one or more non-transitory computer-readable media of claim 23, wherein execution of the instructions is to cause the computer device to facilitate control, by the computing device, of the computing device.

29. The one or more non-transitory computer-readable media of claim 23, wherein, to facilitate control, execution of the instructions is to cause the computer device to facilitate control via one or more of: a cellphone, smartphone, tablet, personal digital assistant ("PDA") or a personal computer.

30. The one or more non-transitory computer-readable media of claim 23, wherein, to facilitate control, execution of the instructions is to cause the computer device to provide a user interface to facilitate control of the apparatus.

* * * * *